United States Patent
Levorse, Jr. et al.

(10) Patent No.: US 9,732,304 B2
(45) Date of Patent: Aug. 15, 2017

(54) 3-(CYCLOHEX-1-EN-1-YL)PROPIONATES AND THEIR USE IN PERFUME COMPOSITIONS

(71) Applicant: International Flavors & Fragrances Inc., New York, NY (US)

(72) Inventors: Anthony T. Levorse, Jr., Westfield, NJ (US); Nicole L. Giffin, Hazlet, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 15/422,522

(22) Filed: Feb. 2, 2017

(65) Prior Publication Data

US 2017/0145343 A1  May 25, 2017

Related U.S. Application Data

(63) Continuation of application No. 14/057,147, filed on Oct. 18, 2013, now Pat. No. 9,611,442.

(51) Int. Cl.
*C11B 9/00* (2006.01)

(52) U.S. Cl.
CPC .................................. *C11B 9/0034* (2013.01)

(58) Field of Classification Search
CPC ...... A61K 8/37; A61Q 13/00; C07C 2101/16; C07C 69/608; C11D 3/50
See application file for complete search history.

(56) References Cited

PUBLICATIONS

Joung et al., "Coupling Reaction of Alkenes with a-Bromo Carboxylic Acid Derivatives Using Nickel Boride and Borohydride Exchange Resin in Methanol", 1988, J. Org. Chem., vol. 63, pp. 2755-2757.*

* cited by examiner

*Primary Examiner* — Michael B Pallay
(74) *Attorney, Agent, or Firm* — Martin Zhang; XuFan Tseng; Elizabeth M. Stover

(57) ABSTRACT

The present invention pertains to the use of 3-(cyclohex-1-en-1-yl)propionates in enhancing, improving or modifying the fragrance of perfumes, colognes, toilet waters, fabric care products, personal products, and the like, and in counteracting malodors.

4 Claims, No Drawings

3-(CYCLOHEX-1-EN-1-YL)PROPIONATES AND THEIR USE IN PERFUME COMPOSITIONS

STATUS OF RELATED APPLICATIONS

This application is a continuation of U.S. Ser. No. 14/057,147, filed Oct. 18, 2013, now allowed, the content hereby incorporated by reference as if set forth in its entirety.

FIELD OF THE INVENTION

The present invention relates to novel chemical entities, a method of using the same as fragrance materials and a method of using the same as malodor counteracting materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances. For example, benzene compounds that differ slightly in substituents possess completely different odor profiles [Ishikawa, et al., International Journal of Quantum Chemistry 79: 101-108 (2000)]. In the case of tert-butyl cyclohexanes, the odor is said to be dependent on the compounds' conformation and therefore analogs adopting same conformation possess similar odor. Accordingly, many trans-compounds are shown to share pronounced urine-perspiration-type odor, while the corresponding cis-compounds are odorless or at the most possess weak and undefinable flowery or woody odor. However, some other trans- and cis-tert-butyl cyclohexanes are shown to possess opposite sensory activities [Ohloff, et al., Helvetica Chimica Acta 66, Fasc. 5: 1343-1354 (1983)]. Thus, it is hard for those with skill in the art to predict a given structure would be effective in sensory activities. Identifying desirable fragrance chemicals continues to pose difficult challenges.

Another effort in the fragrance industry has been made to provide new chemicals to treat and control malodors. "Malodor" is a term used to describe undesirable or unpleasant odor. Common sources of malodors include body perspiration, smoke, environmental odor such as mold and mildew, bathroom, and etc. Conventional perfumes including a variety of fragrance materials are developed to mask malodors, which generally function via two mechanisms: first, the fragrance materials blend with the malodor compound to provide a different and more desirable aroma; and second, the fragrance materials are employed to overwhelm the malodor compound. However, a large quantity of fragrance materials is required for both mechanisms, which in itself is often undesirable. Thus, there remains a need for new chemicals that are effective in counteracting malodors.

SUMMARY OF THE INVENTION

The present invention provides novel compounds, the unexpected advantageous use thereof in enhancing, improving or modifying the fragrance of perfumes, colognes, toilet waters, fabric care products, personal products, and the like, and the unexpected advantageous use thereof in counteracting malodors.

One embodiment of the invention relates to novel 3-(cyclohex-1-en-1-yl)propionates represented by Formula I set forth below:

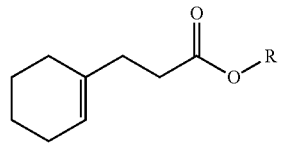

Formula I wherein R is selected from the group consisting of ethyl and 2-propyl.

Another embodiment of the invention relates to a method of improving, enhancing or modifying a fragrance formulation through the addition of an olfactory acceptable amount of the novel 3-(cyclohex-1-en-1-yl)propionates represented by Formula I provided above.

Another embodiment of the invention relates to a fragrance composition comprising the novel 3-(cyclohex-1-en-1-yl)propionates represented by Formula I provided above.

Another embodiment of the invention relates to a method of counteracting a malodor comprising the step of introducing a malodor counteracting effective amount of the novel 3-(cyclohex-1-en-1-yl)propionates represented by Formula I provided above.

Another embodiment of the invention relates to a malodor counteracting composition comprising the novel 3-(cyclohex-1-en-1-yl)propionates represented by Formula I provided above.

These and other embodiments of the present invention will be apparent by reading the following specification.

DETAILED DESCRIPTION OF THE INVENTION

In one embodiment of the present invention, the compounds of the present invention are represented by the following structures:

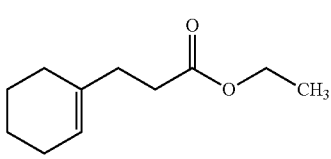

Structure I

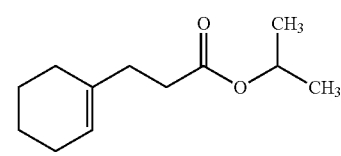

Structure II

Those with skill in the art will recognize that:
Structure I is ethyl 3-(cyclohex-1-en-1-yl)propionate; and
Structure II is 2-propyl 3-(cyclohex-1-en-1-yl)propionate.

The compounds of the present invention can be prepared from bicyclononalactone (commercially available from International Flavors & Fragrances Inc.). The reaction steps can be depicted by a scheme shown as follows:

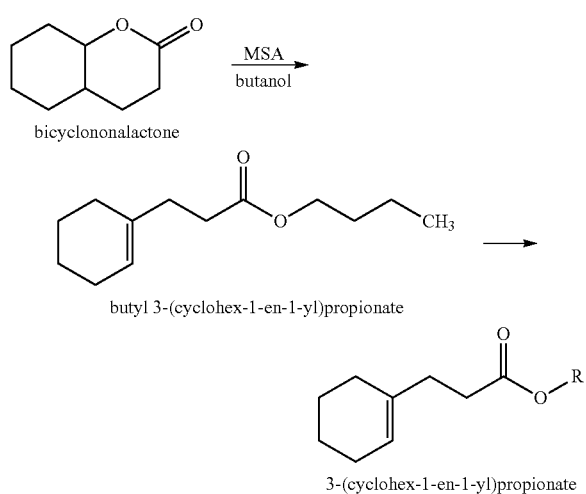

wherein MSA represents methanesulfonic acid; and
wherein R is defined as above.

The above preparation is detailed in the Examples. Materials were purchased from Aldrich Chemical Company unless noted otherwise.

The compounds of the present invention are surprisingly found to possess powerful and complex fragrance effect such as, for example, fruity and woody notes supported by a spiciness aspect.

The use of the compounds of the present invention is widely applicable in current perfumery products, including the preparations of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5 -pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention may comprise a compound of the present invention and further a complementary fragrance compound as defined above.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention may contain a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.05 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole and mmHg be millimeters (mm) of mercury (Hg). IFF as used in the examples is understood to mean International Flavors & Fragrances Inc., New York, N.Y., USA.

EXAMPLE I

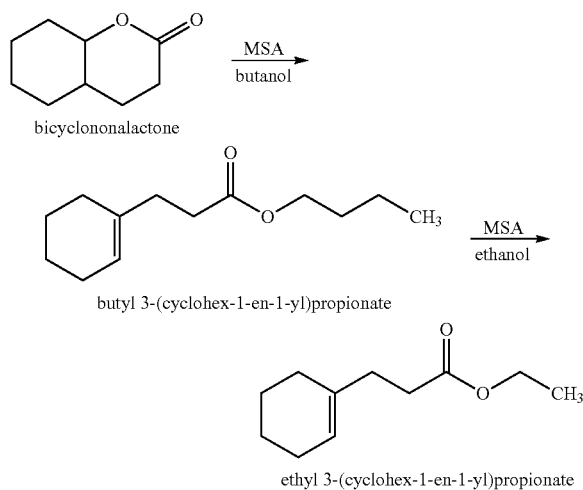

bicyclononalactone butyl 3-(cyclohex-1-en-1-yl)propionate ethyl 3-(cyclohex-1-en-1-yl)propionate Preparation of Ethyl 3-(Cyclohex-1-en-1-yl)propionate (Structure I): A 2-L reaction flask equipped a reflux condenser and a Dean Stark trap was charged with bicyclononalactone (commercially available from IFF) (600 g, 3.89 mol), butanol (432 g, 5.8 mol) and methanesulfonic acid (MSA) (18.7 g, 0.19 mol). The reaction mixture was heated to reflux at 110-120° C. for 4-6 hours. Water (~50 mL) was collected in the Dean Stark trap. The reaction mixture was then cooled to an ambient temperature, neutralized with aqueous sodium carbonate ($Na_2CO_3$) (10%, 100 mL) and washed with brine (1 L). Flash vacuum distillation at a boiling point of 160-175° C. and a pressure of 3 mmHg afforded crude butyl 3-(cyclohex-1-en-1-yl)propionate. Subsequently, a 3-L reaction flask equipped a reflux condenser was charged with the crude butyl 3-(cyclohex-1-en-1-yl)propionate (700 g) from the previous step, ethanol (1 L) and MSA (10 g, 0.1 mol). The reaction mixture was heated to reflux at 80-100° C. for 8 hours. The reaction mixture was then cooled to an ambient temperature, neutralized with aqueous $Na_2CO_3$ (10%, 2 L) and washed with brine (1 L). The organic layer was separated from the aqueous layer in a separatory funnel and further fractional distilled to afford product ethyl 3-(cyclohex-1-en-1-yl)propionate (379 g) with a boiling point of 127-131° C. and a pressure of 3 mmHg.

$^1$H NMR (500 MHz, $CDCl_3$): 5.41 ppm (m, 1H), 4.12 ppm (q, 2H, J=7.15 Hz), 2.40 ppm (t, 2H, J=7.00 Hz), 2.25 ppm (t, 2H, J=7.00 Hz)), 1.90-2.00 ppm (m, 4H), 1.50-1.64 ppm (m, 4H), 1.25 ppm (t, 3H, J=7.15 Hz).

EXAMPLE II

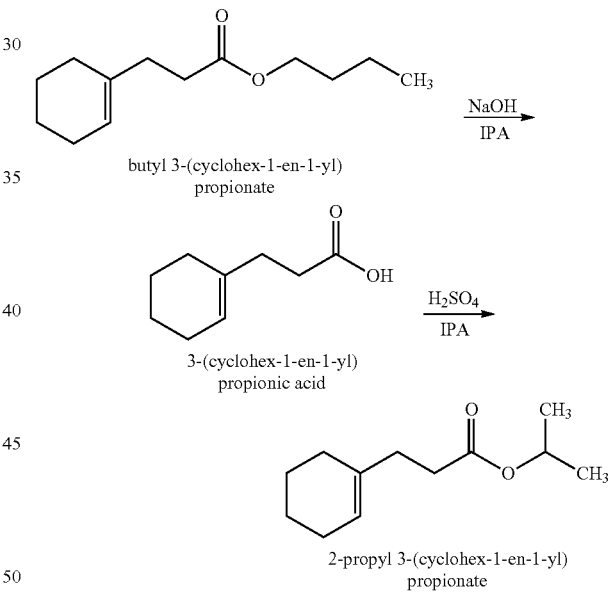

butyl 3-(cyclohex-1-en-1-yl) propionate 3-(cyclohex-1-en-1-yl) propionic acid 2-propyl 3-(cyclohex-1-en-1-yl) propionate Preparation of 2-Propyl 3-(Cyclohex-1-en-1-yl)propionate (Structure II): A 3-L reaction flask equipped a reflux condenser was charged with crude butyl 3-(cyclohex-1-en-1-yl)propionate (421 g, 2 mol) (prepared as above in EXAMPLE I), 2-propanol (IPA) (2 L) and aqueous sodium hydroxide solution (NaOH) (50% by weight) (240 g, 3 mol). The reaction mixture was heated to reflux at 80-85° C. for 8 hours. The reaction mixture was then cooled to an ambient temperature and acidified with hydrochloric acid (HCl) (37%, 400 mL). Toluene (500 mL) was added and the reaction mixture was washed with brine (2 L). The organic layer was removed via a separatory funnel. Toluene was recovered using a Buchi Rotary Evaporator to afford solvent-free crude 3-(cyclohex-1-en-1-yl)propionic acid. Subsequently, a 2-L reaction flask equipped a reflux condenser was charged with the crude 3-(cyclohex-1-en-1-yl)propionic acid from the previous step, IPA (1.5 L) and sulfuric acid (H₂SO₄) (98%, 10 g). The reaction mixture was heated to reflux at 80-85° C. for 4 hours. The reaction was then cooled to an ambient temperature, neutralized with aqueous Na₂CO₃ (10%, 2 L) and washed with brine (1 L). The organic layer was separated from the aqueous layer in a separatory funnel and further fractional distilled to afford product 2-propyl 3-(cyclohex-1-en-1-yl)propionate (20 g) with a boiling point of 124-128° C. and a pressure of 3 mmHg.

¹H NMR (500 MHz, CDCl₃): 5.41 ppm (m, 1H), 5.00 ppm (hep, 1H, J=6.25 Hz), 2.37 ppm (t, 2H, J=7.60 Hz), 2.24 ppm (t, 2H, J=7.60 Hz), 1.90-2.00 ppm (m, 4H), 1.50-1.64 ppm (m, 4H), 1.22 ppm (d, 6H, J=6.25 Hz)

EXAMPLE III

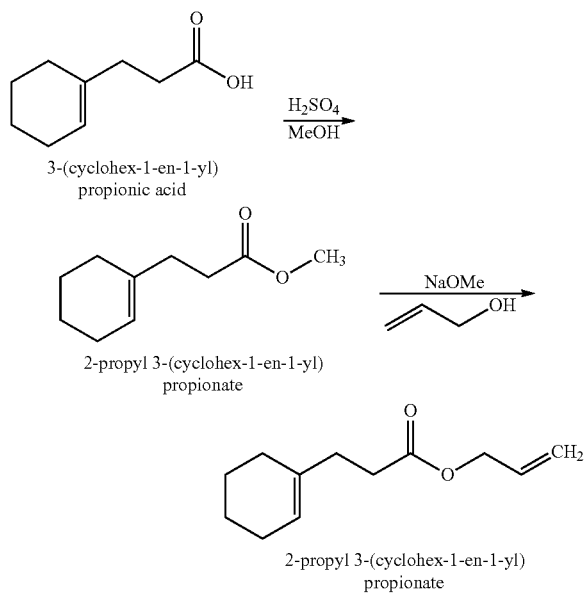

Preparation of Allyl 3-(cyclohex-1-en-1-yl)propionate (Structure III): A 3-L reaction flask equipped a reflux condenser was charged with crude 3-(cyclohex-1-en-1-yl)propionic acid (400 g, 2.5 mol) (prepared as above in EXAMPLE II), methanol (MeOH) (2 L) and H₂SO₄ (98%, 18 g). The reaction mixture was heated to reflux at 65-75° C. for 8 hours. The reaction mixture was then cooled to an ambient temperature and diluted with toluene (500 mL). The reaction mixture was neutralized with aqueous Na₂CO₃ (10%, 2 L) and washed with brine (1 L) to obtain crude methyl 3-(cyclohex-1-en-1-yl)propionate. Subsequently, a 2-L reaction flask equipped a reflux condenser and a Dean Stark trap was charged with the crude methyl 3-(cyclohex-1-en-1-yl)propionate from the previous step, allyl alcohol (CH₂=CHCH₂OH) (282 g, 4.8 mol) and sodium methoxide (NaOMe) (11 g, 0.2 mol). The reaction mixture was heated to reflux at 65-85° C. for 8 hours. Methanol was removed. The reaction was then cooled to an ambient temperature, neutralized with aqueous acetic acid (10%, 2 L) and washed with brine (1 L). The organic layer was separated from the aqueous layer in a separatory funnel and further fractional distilled to afford product allyl 3-(cyclohex-1-en-1-yl)propionate (20 g) with a boiling point of 140-146° C. and a pressure of 3 mmHg.

¹H NMR (500 MHz, CDCl₃): 5.86-5.95 ppm (m, 1H), 5.42 ppm (m, 1H), 5.20-5.34 ppm (m, 2H), 4.57 ppm (d, 2H, J=5.65 Hz), 2.44 ppm (t, 2H, J=7.75 Hz), 2.26 ppm (t, 2H, J=7.75 Hz), 1.90-2.00 ppm (m, 4H), 1.50-1.64 ppm (m, 4H)

EXAMPLE IV

Ethyl 3-(cyclohex-3-en-1-yl)propionate (Structure IV):

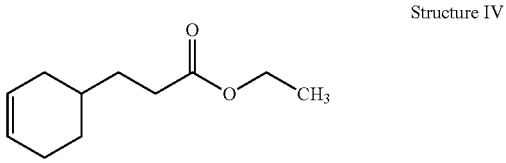

¹H NMR (500 MHz, CDCl₃): 5.57-5.49 ppm (bs, 2H), 4.10 ppm (t, 2H, J=7.15 Hz), 2.63-2.55 ppm (m, 2H), 2.32 ppm (t, 2H, J=7.00 Hz)), 2.20-1.40 ppm (m, 7H), 1.18 ppm (t, 3H, J=7.15 Hz)

Allyl 3-(cyclohex-3-en-1-yl)propionate (Structure V):

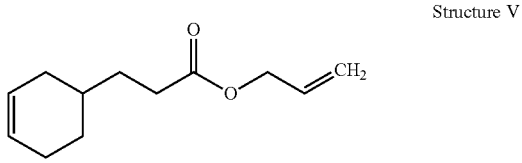

¹H NMR (500 MHz, CDCl₃): 5.57-5.49 ppm (bs, 2H), 5.42 ppm (m, 1H), 5.20-5.34 ppm (m, 2H), 4.57 ppm (d, 2H, J=5.65 Hz), 2.44 ppm (t, 2H, J=7.75 Hz), 2.26 ppm (t, 2H, J=7.75 Hz), 2.20-1.40 ppm (m, 7H)

Methyl 3-(cyclohex-1-en-1-yl)propionate (Structure VI):

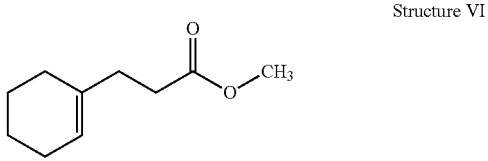

¹H NMR (500 MHz, CDCl₃): 5.41 ppm (m, 1H), 3.60 ppm (s, 3H), 2.40 ppm (t, 2H, J=7.00 Hz), 2.25 ppm (t, 2H, J=7.00 Hz), 1.90-2.00 ppm (m, 4H), 1.50-1.64 ppm (m, 4H)

Methyl 3-(cyclohex-3-en-1-yl)propionate (Structure VII):

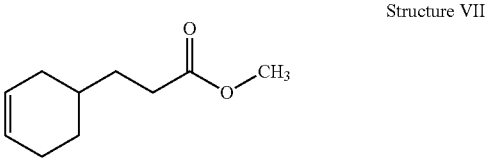

$^1$H NMR (500 MHz, CDCl$_3$): 5.57-5.49 ppm (bs, 2H), 3.66 ppm (s, 3H), 2.63-2.55 ppm (m, 2H), 2.32 ppm (t, 2H, J=7.00 Hz)), 2.20-1.40 ppm (m, 7H)

EXAMPLE V

The above compounds (i.e., Structures I-VII) were evaluated for odor properties.

| Chemical Name | Compound | Odor Profile |
| --- | --- | --- |
| Ethyl 3-(cyclohex-1-en-1-yl)propionate (Structure I) | | Powerful and complex with unique fruity and woody combination. The woody aspect, supported by spiciness, provided further dimension. |
| 2-Propyl 3-(cyclohex-1-en-1-yl)propionate (Structure II) | | Fruity and sweet but less powerful and complex than Structure I. |
| Allyl 3-(cyclohex-1-en-1-yl)propionate (Structure III) | | Fruity and green but unpleasant. Chemical, dirty and artificial. |
| Ethyl 3-(cyclohex-3-en-1-yl)propionate (Structure IV) | | Fruity but dirty and unpleasant. As dried, fruitiness dissipated quickly and a sweaty and cumin-like character became predominant |
| Allyl 3-(cyclohex-3-en-1-yl)propionate (Structure V) | | Fruity but with dirty metal and potato skin characters. |
| Methyl 3-(cyclohex-1-en-1-yl)propionate (Structure VI) | | Less appealing, weaker and less complex than Structure I. |
| Methyl 3-(cyclohex-3-en-1-yl)propionate (Structure VII) | | Less appealing, weaker and less complex than Structure I and slightly metallic. |

Among Structures I-VII, Structures I and II exhibited desirable odors. In particular, Structure I possessed strong and complex odors, superior to the others. The advantageous properties of Structures I and II are unexpected.

EXAMPLE VI

Establishment of Malodor Models: A number of malodorous chemicals have been identified, which are associated with different types of malodors. Commercial samples of these chemicals (commercially available at Sigma-Aldrich Inc.) were thus used in the present invention as malodorous model compounds to assess the effectiveness of ethyl 3-(cyclohex-1-en-1-yl)propionate in counteracting malodors.

A model of bathroom malodor was established using a solution of isovaleric acid ("IVA"). A model of sweat malodor was established using a solution of 3-methyl-2-hexanoic acid. A model of mold/mildew malodors was established using a solution of 2-ethyl-1-hexanol. A model of smoke malodor was established by applying a solution of 3-acetyl pyridine.

Preparation of Test Samples: Ethyl 3-(cyclohex-1-en-1-yl)propionate was prepared at a series of concentrations, ranging from 0.1% to 10% in diethyl phthalate ("DEP").

A malodor material as established above (1 g) and a solution of ethyl 3-(cyclohex-1-en-1-yl)propionate in DEP (1 g) (1%) were pipetted into separate aluminum weighing dishes located at the bottom of a 32 oz. jar (1 L). For negative control samples (Malodor Alone), the malodor material (0.5 g) was pipetted into each of the two dishes located at the bottom of jar. Jars were then capped and the samples were allowed to equilibrate for 24 hours before testing.

Testing Procedure: Test samples were presented in a blind and pseudorandom order to a group of trained panelists (consisting of 20 females with a mean age of 45 years). The panelists were instructed to take the following steps: i) sniff malodor reference jars for familiarization prior to each testing session; ii) uncap a jar; iii) place their noses at a distance of about 3-4 inches above the opening; iv) take short sniffs for about 2-3 seconds; and v) enter a rating of overall intensity and malodor intensity on a handheld computer.

The overall and malodor intensity was rated using the Labeled Magnitude Scale (LMS) [Green, et al., Chemical Senses, 21(3): 323-334 (1996)]. Mean ("Malodor Intensity") and standard error of the mean ("SE", ±) were obtained, where 0 represents "No Sensation" and 100 represents "The Strongest Imaginable Malodor Sensation". Percent malodor reduction ("% MOR") represents the perceived reduction in mean malodor intensity of the sample containing the malodor in the presence of methyl 3-methyl cyclohexane carboxylate relative to the negative control (Malodor Alone).

Test Results: The malodor test results are as follows:

| No. | Group | % MOR |
| --- | --- | --- |
| 1 | Sweat Malodor | 86 |
| 2 | Bathroom Malodor | 79 |
| 3 | Mold/Mildew Malodor | 78 |
| 4 | Smoke Malodor | 88 |

The above test has demonstrated the effectiveness of 3-(cyclohex-1-en-1-yl)propionate in counteracting various types of malodor including sweat, bathroom, mold/mildew and smoke.

What is claimed is:

1. A method of improving, enhancing or modifying a fragrance formulation through the addition of an olfactory acceptable amount of a compound of formula:

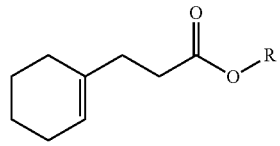

wherein R is selected from the group consisting of ethyl and 2-propyl.

2. The method of claim 1, wherein the olfactory acceptable amount is from about 0.005 to about 50 weight percent of the fragrance formulation.

3. The method of claim 1, wherein the olfactory acceptable amount is from about 0.5 to about 25 weight percent of the fragrance formulation.

4. The method of claim 1, wherein the olfactory acceptable amount is from about 1 to about 10 weight percent of the fragrance formulation.

* * * * *